(12) United States Patent
Cho et al.

(10) Patent No.: US 6,924,642 B1
(45) Date of Patent: Aug. 2, 2005

(54) MAGNETORESTRICTIVE TRANSDUCER FOR GENERATING AND MEASURING ELASTIC WAVES, AND APPARATUS FOR STRUCTURAL DIAGNOSIS USING THE SAME

(75) Inventors: Seung Hyun Cho, Gyeonggi-do (KR); Kyung Ho Sun, Kwangju (KR); Ju Seung Lee, Kyeongsangbuk-do (KR); Yoon Young Kim, Seoul (KR)

(73) Assignee: Seoul National University Industry Foundation (KR)

( * ) Notice: Subject to any disclaimer, the term of this patent is extended or adjusted under 35 U.S.C. 154(b) by 0 days.

(21) Appl. No.: 10/958,269

(22) Filed: Oct. 6, 2004

(30) Foreign Application Priority Data

Apr. 22, 2004 (KR) ................. 10-2004-0027928

(51) Int. Cl.[7] .............................................. G01N 27/82
(52) U.S. Cl. ...................................... 324/240; 324/220
(58) Field of Search ................................ 324/219–220, 324/228, 232, 234, 238–241, 242–244, 260; 73/584, 627, 643

(56) References Cited

U.S. PATENT DOCUMENTS 4,295,214 A * 10/1981 Thompson .................. 367/140
6,624,628 B1 * 9/2003 Kwun et al. ................ 324/240

* cited by examiner

Primary Examiner—Bot LeDynh
(74) Attorney, Agent, or Firm—Dickstein Shapiro Morina & Oshinsky LLP

(57) ABSTRACT

Disclosed is a magnetostrictive transducer for generating and receiving elastic waves in a testing plate and an apparatus for structural diagnosis using the magnetostrictive transducers. More particularly, disclosed is a magnetostrictive transducer which may generate and transmit elastic waves using the magnetostrictive effect in any directions without re-attaching ferromagnetic patch on the non-magnetic testing plate and may produce Lamb waves and Shear Horizontal (SH) waves in desired directions, and an apparatus for structural diagnosis using the magnetostrictive transducers.

There is provided a magnetostrictive transducer comprising: a patch made of ferromagnetic material; and a magnetic field generator for generating magnetic field applied to the patch, the magnetic field generator being placed on the patch, wherein the magnetic field generator comprises: a main body; two magnets for generating bias magnetic field, the magnets being apart from each other; and a coil for winding around the magnets.

13 Claims, 10 Drawing Sheets

MAGNETORESTRICTIVE TRANSDUCER FOR GENERATING AND MEASURING ELASTIC WAVES, AND APPARATUS FOR STRUCTURAL DIAGNOSIS USING THE SAME

CROSS-REFERENCE TO RELATED APPLICATIONS

The entire disclosure of Korean Patent Application No.10-2004-0027928 filed on Apr. 22, 2004 including specification, claims, drawings and summary, is incorporated herein by reference in its entirety.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

1. Field of the invention

The present invention relates to a magnetostrictive transducer for generating and receiving elastic waves in a testing plate and an apparatus for structural diagnosis using the magnetostrictive transducers. More particularly, the present invention relates to a magnetostrictive transducer which may generate and transmit elastic waves using the magnetostrictive effect in any directions without re-attaching ferromagnetic patch on the non-magnetic testing plate and may produce Lamb waves and Shear Horizontal (SH) waves in desired directions, and an apparatus for structural diagnosis using the magnetostrictive transducers.

2. Description of the Related Art

Magnetostrictive effect, which is also called Joule effect, refers to a phenomenon that mechanical deformation occurs in a ferromagnetic material when the ferromagnetic material is placed in magnetic fields. A reciprocal phenomenon of the magnetostrictive effect (i.e. a phenomenon that changes in magnetic field in vicinity of materials occur when mechanical stress is applied to the materials) is designated as inverse magnetostrictive effect or Villari effect.

The magnetostrictive effect can be expressed as follows.

When ferromagnetic materials are placed in magnetic field H, induced magnetic flux density B inside the ferromagnetic materials is the sum of magnetic flux density in vacuum and magnetic flux density induced by magnetization of the ferromagnetic materials. Therefore, the magnetic flux density B inside the ferromagnetic materials can be expressed as equation 1.

$$B = \mu_0 H + \mu_0 M = \mu_0 H + \mu_0 \chi_m H = \mu_0 (1+\chi_m) H = \mu_0 \mu_r H = \mu H \quad \text{Equation 1}$$

where B denotes magnetic flux density, H denotes magnetic field intensity applied by an outside magnet or electromagnet, M denotes magnetization, $\chi_m$ denotes magnetic susceptibility, $\mu_0$ denotes permeability of free space, $\mu_r$ denotes relative permeability, and $\mu$ denotes permeability.

The Villari effect and Joule effect can be expressed as equations 2 and 3.

$$\varepsilon = \frac{\sigma}{E^H} + q*H. \quad \text{Equation 2}$$

$$B = \mu^\sigma H + q\sigma \quad \text{Equation 3}$$

where $\varepsilon$ denotes strain, $\sigma$ denotes stress applied to the ferromagnetic material, $E^H$ denotes modulus of elasticity in a constant magnetic field and $\mu^\sigma$ denotes permeability when constant stress is applied.

The coefficients q* and q in equations 2 and 3 representing the Villari effect and Joule effect can be represented as equations 4 and 5, respectively.

$$q^* = \frac{d\varepsilon}{dH}\bigg)_\sigma. \quad \text{Equation 4}$$

$$q = \frac{dB}{d\sigma}\bigg)_H. \quad \text{Equation 5}$$

Transducers using such magnetostrictive effect are applied in various fields because it is possible for the transducers to measure deformation of objects to be measured without physical contact with the objects. According to the magnetostrictive effect, it is possible to generate elastic waves without physical contact with objects to be measured and to generate elastic waves larger than waves generated using piezoelectric effect in the related art.

Generally, elastic guided waves in a plate can be classified into Lamb waves and SH waves with regard to vibrating way of particles. Lamb waves refer to elastic waves vibrating a particle in a plane, parallel to direction of wave propagation and vertical to a plate, and SH waves means elastic waves vibrating a particle vertically to the direction of wave propagation in a plane parallel to the plate. Especially, since a first mode of the SH waves travel without collision with lower and upper interfaces of the plate, it is non-dispersive and can propagate with high efficiency.

FIGS. 1a and 1b illustrate a general configuration of an apparatus for generating elastic waves in the related art. As illustrated in FIGS. 1a and 1b, the apparatus includes: a thin ferromagnetic strip 1 adhered on a plate 2 using a couplant 4, a plate magnetostrictive probe 5 mounted on the ferromagnetic strip 1.

In the apparatus for generating elastic waves in the related art, the ferromagnetic strip 1 is adhered on the plate 2, and introduction of currents to the probe induces magnetic field with flux lines vertically entering and radially emitting out the ferromagnetic strip 1. Therefore, a change in rectangular ferromagnetic strip through the magnetostrictive effect mainly occurs in a direction of its length. Consequently, once the apparatus for generating elastic waves in the related art is installed, a direction of generated elastic waves is permanently fixed. So, in order to change a direction of elastic waves propagation, it is needed to detach the ferromagnetic strip 1 from the plate 2 and re-attach the ferromagnetic strip 1 on the plate 2 in a desirable direction. However, occasionally, it is impossible to detach and re-attach the ferromagnetic strip when defects of an inaccessible structure are to be inspected. Thus, it is difficult to use the apparatus of the related art for generating elastic waves in a desired direction.

Since maximum deformation occurs in a direction of magnetic field according to the magnetostrictive effect, it is desirable that magnetic field applied to the ferromagnetic strip is generated in a direction of elastic waves propagation. However, the apparatus for generating elastic waves in the related art generates magnetic field with flux lines vertically entering and radially emitting out the ferromagnetic strip, so that it is not effective to enlarge output of the elastic waves.

Moreover, it has a drawback that a plurality of apparatuses for generating elastic waves are required for two dimensional inspection of defects in objects to be inspected, since the direction of elastic waves propagation is fixed once the apparatus in the related art is installed.

Further, the apparatus in the related art has another drawbacks that it needs pre-magnetization every single run and it is difficult to control size of pre-magnetization and elastic waves, because pre-magnetization of the ferromagnetic strip through using permanent magnets should be performed before applying additional magnetic field through the coil in order to generate SH waves.

Therefore, there is a need for a more efficient magnetostrictive transducer which may generate elastic waves in a desired direction without re-attaching a ferromagnetic strip thereof and may generate bias and additional magnetic fields in same direction. Further, there is a need for an apparatus for structural diagnosis using such transducers which may perform two dimensional inspection of defects in a wide plate.

BRIEF SUMMARY OF THE INVENTION

Accordingly, the present invention has been made to solve the above-mentioned problems occurring in the related art, and an object of the present invention is to provide a magnetostrictive transducer which may easily generate elastic waves in a desired direction and may apply efficiently magnetic fields.

Further object of the present invention is to provide a magnetostrictive transducer which may generate Lamb waves and SH waves in desired directions.

Further, another object of the present invention is to provide an apparatus for structural diagnosis which may perform two dimensional inspection of defects in a wide plate by making such magnetostrictive transducer generate and measure elastic waves at the same. time and making the magnetostrictive transducer generate elastic waves in any directions. Herein, the apparatus for structural diagnosis uses one magnetostrictive transducer as a transducer for generating elastic waves and uses another magnetostrictive transducer as a transducer for measuring the elastic waves.

In order to accomplish these objects, there is provided a magnetostrictive transducer comprising: a patch having predetermined thickness, the patch being made of ferromagnetic material; and a magnetic field generator for generating magnetic field applied to the patch, the magnetic field generator being placed above the patch, wherein the magnetic field generator comprises: a main body made of non-magnetic material; two magnets for generating bias magnetic field applied to the patch, the magnets being located in upper part of the main body, the magnets being apart from each other; and a coil for winding around the magnets, and wherein as an alternating current is supplied to the coil, additional magnetic field applied to the patch is generated, and the bias magnetic field and the additional magnetic field are parallel to the patch, and wherein, as an alternating current is supplied to the cod, the patch generates Lamb waves in direction of the magnetic field and shear horizontal (SH) waves in direction forming predetermined angle with the direction of the magnetic field.

Preferably, a change in magnetic field applied to the patch can be detected through the magnetic field generator.

Because both the bias magnetic field and the additional magnetic field are parallel to the patch, size of outputs (e.g., elastic waves) can be enlarged.

Preferably, the magnetic field generator is rotatable to change the directions of the Lamb waves and the SH waves. Preferably, the patch may be a circular patch.

Preferably, the cod may be wound around the two magnets in shape of "8."

Preferably, a first magnet of the two magnets may put N pole down and a second magnet of the two magnets may put N pole up, whereby the magnetic fields generated by the two magnets may be parallel to the patch.

Preferably, the magnetic field generator may be placed on the patch.

Differently, there is provided an apparatus for structural diagnosis using magnetostrictive transducers comprising: two magnetostrictive transducers, each of the two magnetostrictive transducers comprising a patch made of ferromagnetic material and a magnetic field generator placed on the patch for generating magnetic field applied to the patch; a power source for supplying electric currents to the magnetostrictive transducer; and a measuring unit for measuring voltage output of the magnetostrictive transducer, wherein the magnetic field generator may comprise: a main body made of non-magnetic material; two magnets for generating bias magnetic field applied to the patch, the magnets being located in upper part of the main body, the magnets being apart from each other; and a coil for winding round the magnets, wherein, as an alternating current is supplied to the coil of a first transducer of the two transducers, the patch may generate Lamb waves in direction of the magnetic field and shear horizontal (SH) waves in direction forming predetermined angle with the direction of the magnetic field, wherein, as the patch of the second transducer goes through mechanical deformation due to the Lamb waves or the SH waves from the first transducer, the magnetic field of the second transducer may vary and amount of the voltage across the coil of the second transducer may vary due to the variation of the magnetic field, and wherein defects of testing plate existing in traveling route of the Lamb waves or the SH waves from the first transducer may be detected by the measuring unit's measuring the voltage variation across the coil of the second transducer.

Preferably, the magnetic field generators are rotatable to change the directions of Lamb waves and SH waves.

Preferably, the patches of the magnetostrictive transducers may be circular patches.

Preferably, the coil may be wound around the two magnets in shape "8."

Preferably, a first magnet of the two magnets may put N pole down and a second magnet of the two magnets may put N pole up, whereby the magnetic fields generated by the two magnets may be parallel to the patch.

Preferably, the magnetic field generator may be placed on the patch.

BRIEF DESCRIPTION OF THE DRAWINGS

The above and other objects, features and advantages of the present invention will be more apparent from the following detailed description taken in conjunction with the accompanying drawings, in which:

FIG. 1b is a cross-sectional view taken along line A—A of FIG. 1a;

DETAILED DESCRIPTION OF THE INVENTION

Hereinafter, a preferred embodiment of the present invention will be described with reference to the accompanying drawings.

Figure 1A:
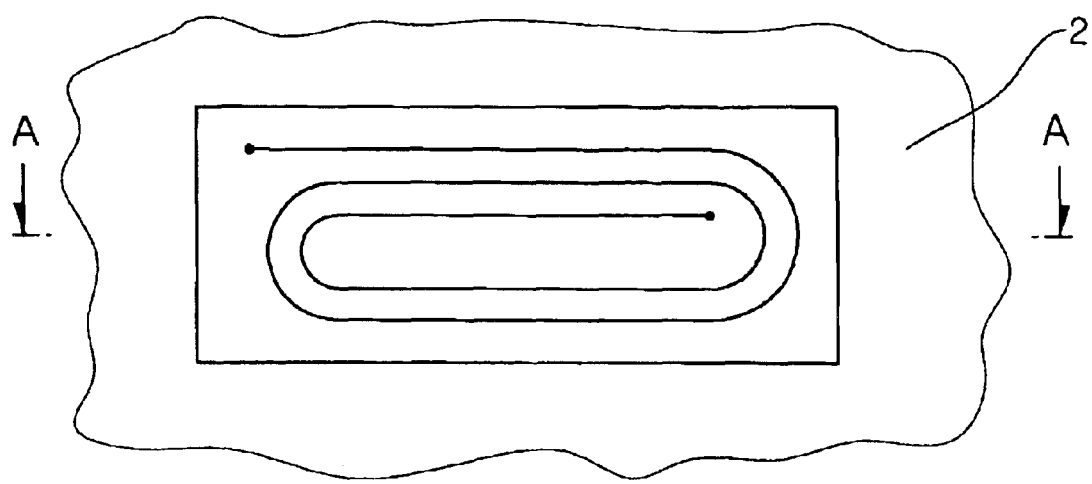
FIG. 1a illustrates a configuration of a magnetostrictive transducer for generating elastic waves in the related art.
Figure 1B:
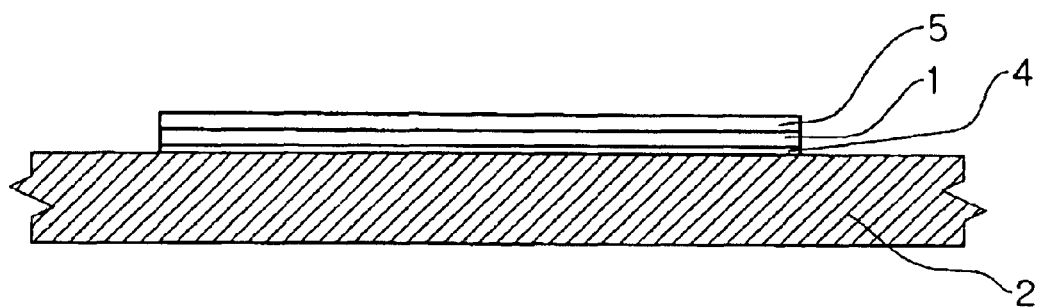
Figure 2:
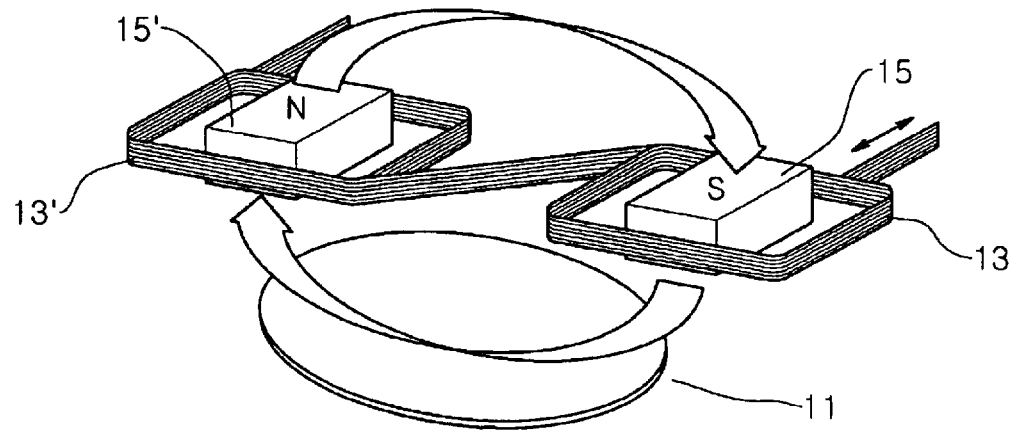
FIG. 2 is a schematic representation illustrating a principle of the transducer according to the present invention.

FIG. 2 illustrates a general configuration of a transducer according to the present invention. A transducer according to the present invention, as illustrated in FIG. 2, comprises: a patch 11 adhered on one side of a plate, a pair of magnets 15 and 15' separated from each other and positioned over the patch 11, and coils 13 and 13' wound around the magnets 15 and 15'.

Figure 3:
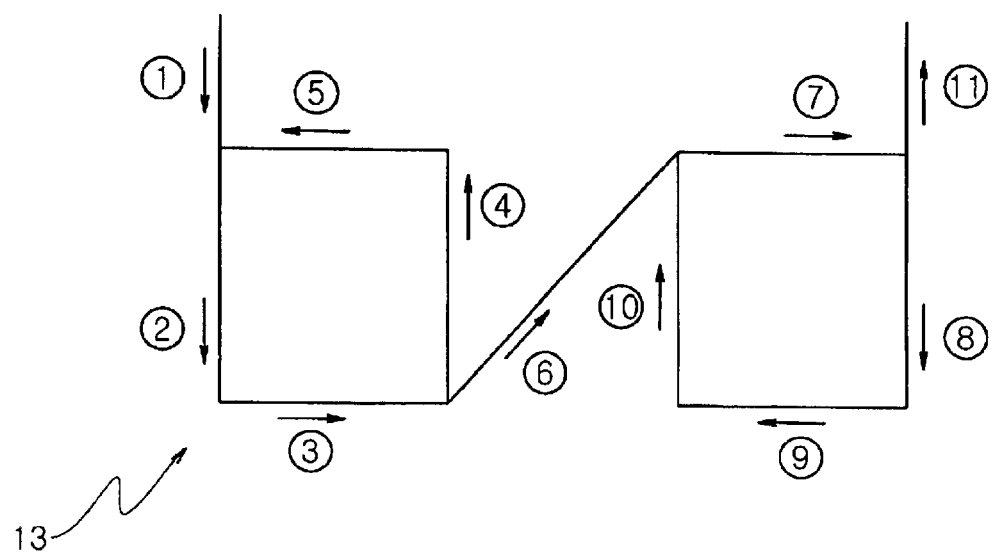
FIG. 3 illustrates schematically a coil construction in the transducer shown in FIG. 2.

FIG. 3 illustrates winding method for "8"-shaped coil. As illustrated in FIG. 3, winding method to form "8"-shaped coil of the transducer according to the present invention comprises the acts of extending a coil from a power source to a first magnet of two magnets(.); winding the coil around the first magnet(.->•); repeating winding for desired turns(.->•); extending the coil to a second magnet(.); winding the coil around the second magnet(.->•); repeating winding for the same turns as used in the first magnet(.->•); and extending the coil to the power source(.).

Figure 4:
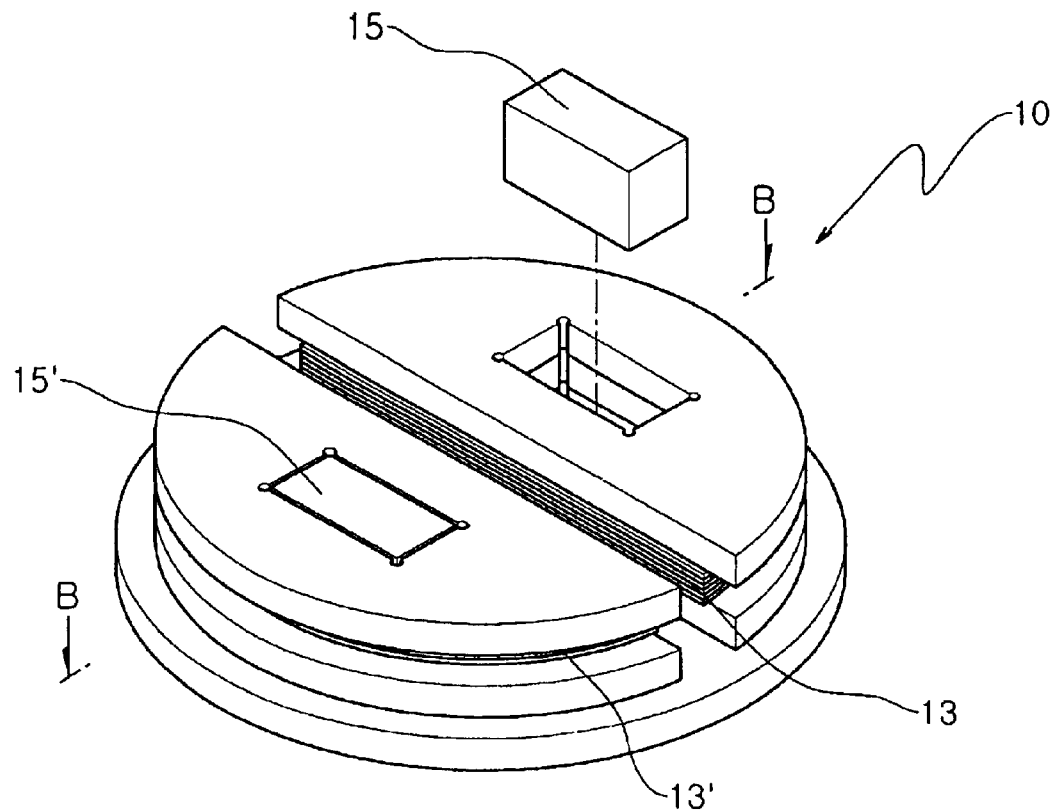
FIG. 4 illustrates a construction of a transducer according to the embodiment of the present invention.
Figure 5:
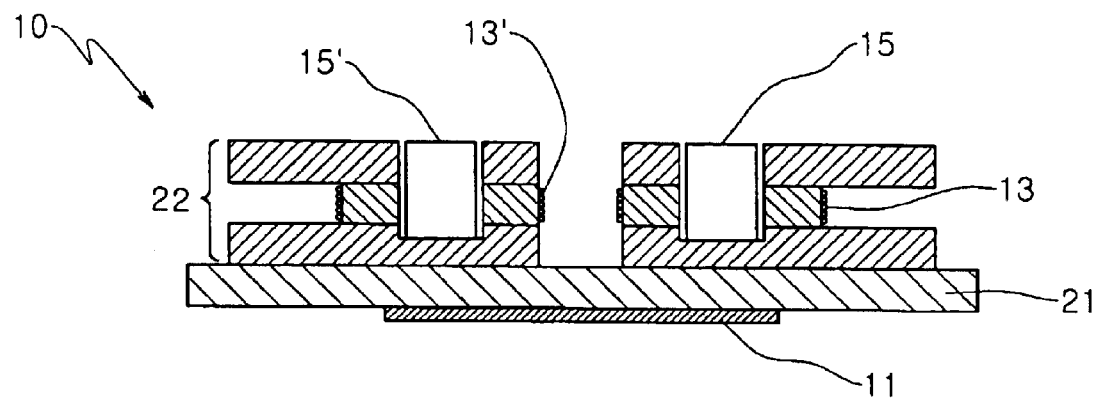
FIG. 5 is a cross-sectional view taken along line B—B of FIG. 4.

FIG. 4 illustrates a configuration of a transducer according to the embodiment of the present invention, illustrated in FIGS. 2 and 3, and FIG. 5 is a cross-sectional view taken along line B—B of FIG. 4.

As illustrated in FIGS. 4 and 5, the transducer according to the present invention comprises: a plate-shaped main body 21 having parallel upper and lower surfaces, a patch 11 placed under the lower surface of the main body 21, two magnets 15 and 15' separated from each other for applying magnetic field to the patch 11, and coil 13 and 13' wound around the magnets 15 and 15' for changing magnetic field applied by the magnets.

The coil 13 and 13' is wound around the magnets 15 and 15' to form the shape of "8". The main body is rotatable and the main body could be placed apart from the patch.

Magnetic field generator 22 is placed on upper surface of the main body 21. The magnetic field generator 22 comprises two magnets 15 and 15', and coil 13 and 13' wound around the two magnets. The first magnet 15 of the two magnets puts N pole down and the second magnet 15' of two magnets puts S pole down. Therefore, magnetic fields are produced to be applied to the patch with magnetic flux lines parallel to the patch, as illustrated in FIG. 2.

Preferably, the patch 11 is made of ferromagnetic materials like nickel, and a part retaining the magnets and the coil in the magnetic field generator is made of non-magnetic materials like acryl.

Figure 6:
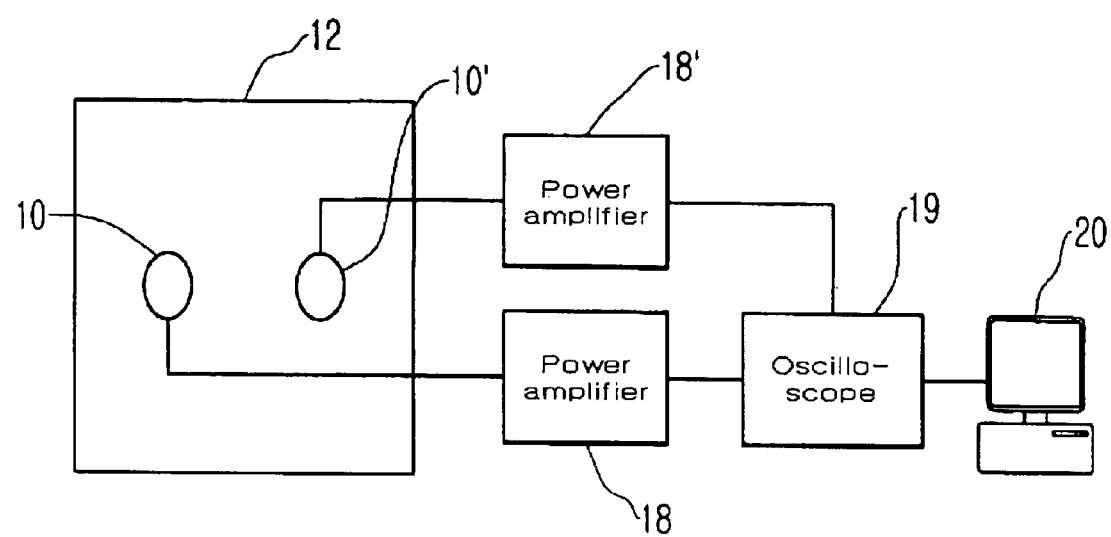
FIG. 6 illustrates a configuration of an apparatus for structural diagnosis according to the present invention.

FIG. 6 illustrates a configuration of an apparatus for structural diagnosis according to the present invention, using a transducer explained above.

As illustrated in FIG. 6, an apparatus for structural diagnosis according to the present invention comprises an elastic waves generating unit 10 for generating elastic waves through the magnetostrictive effect, the elastic waves generating unit 10 being placed above or on a patch placed on a plate, an elastic waves receiving unit 10' for measuring the elastic waves generated by the elastic waves generating unit 10, the elastic waves receiving unit 10' being placed above or on a parch placed on the plate, two power amplifiers 18 and 18' for supplying electric currents to the elastic waves generating unit 10 and the elastic waves receiving unit 10', an oscilloscope 19 for digitizing a variation of currents detected at the elastic waves receiving unit 10' in proportion to the elastic waves generated by the elastic waves generating unit 10, and a computer 20 for processing the digitized data received from the oscilloscope.

Both the elastic waves generating unit and the elastic waves receiving unit have the same configuration as the transducer according to the present invention. That is, the transducer according to the present invention can be used as both the elastic waves generating unit and the elastic waves receiving unit.

Two power amplifiers 18 and 18' can be replaced by one power amplifier which outputs two respective outputs, and simultaneously act as a power source for direct or alternating currents and an amplifier to amplify a signal.

Hereinafter, a method of detecting structural defects of a plate by using such apparatus for structural diagnosis will be described.

As illustrated in FIG. 6, an elastic waves generating unit 10 and an elastic waves receiving unit 10' are placed respectively above or on a plate, and then arc energized with electric currents through the power amplifiers 18 and 18'. If the electric current is supplied to the elastic waves generating unit 10, bias magnetic field generated by bias magnets and additional magnetic field generated by the electric currents flowing through the coil are applied to the patch 11 at the same time. In other words, the electric current flowing through the coil 13 and 13' changes magnetic field applied to the patch 11. Thus, the patch, ferromagnetic material, is deformed according to the magnetostrictive effect and elastic waves are generated and transmitted to the plate. If elastic waves are transmitted to the elastic waves receiving unit, patch of the elastic waves receiving unit is deformed, thereby changing amount of magnetic field of the elastic waves receiving unit. The variation of the magnetic field generates electromotive force across the coil 13 and 13' of the elastic waves receiving unit. Amount of the electromotive force is measured and the electromotive force is amplified by the amplifier 18. The amplified electromotive force is transmitted to the oscilloscope 19 and the personal computer 20 to be processed.

As mentioned above, since main bodies are freely rotatable on the respective patches of the elastic waves generating unit 10 and elastic waves receiving unit 10' having the same configuration as the transducer according to the present invention, it is possible to control propagating direction of elastic waves generated by the elastic waves generating unit 10.

Figure 7:
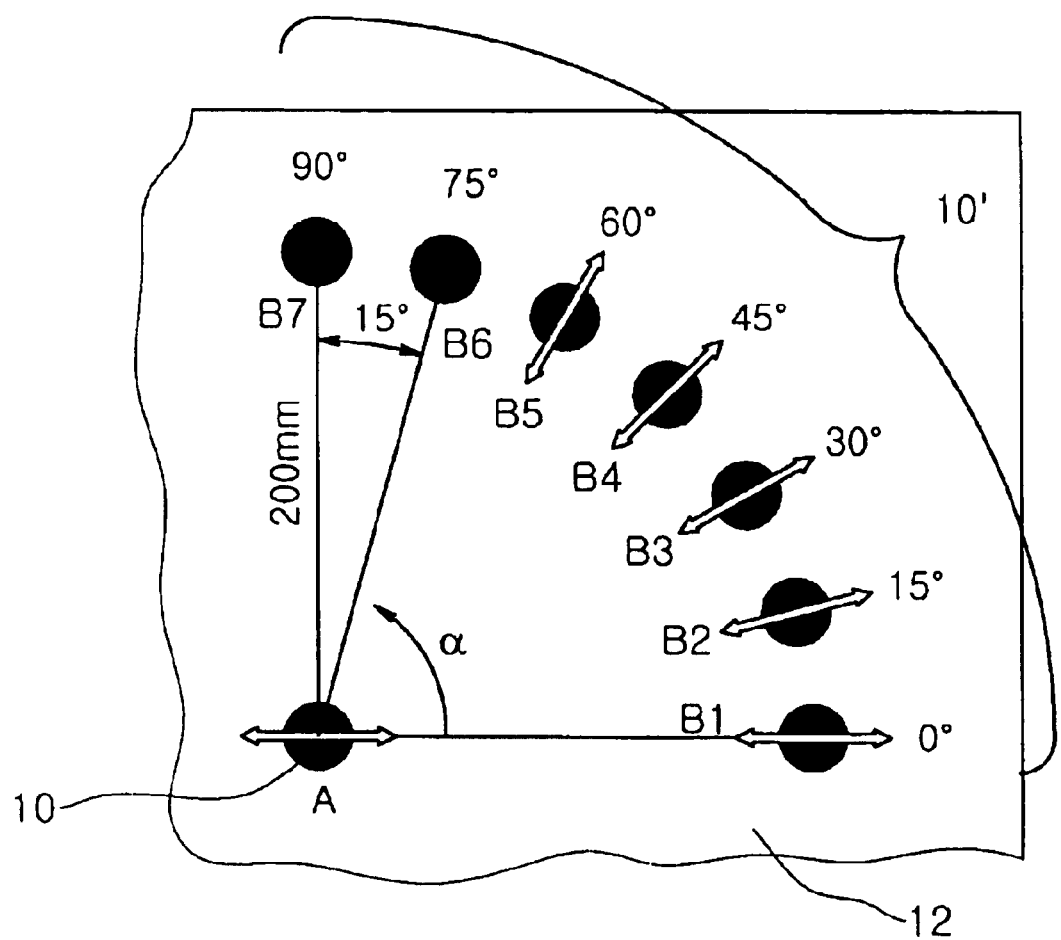
FIG. 7 illustrates a configuration of experiments for analyzing directional features of a transducer according to the present invention.

FIG. 7 illustrates a configuration of experiment for analyzing directional features of the transducer according to the present invention.

As illustrated in FIG. 7, the elastic waves generating unit 10 for generating elastic waves is placed above or on upper surface of a testing plate and seven receiving units 10' are placed above or on the plate predetermined distance (for example, 200 mm) apart from the elastic waves generating unit 10. Meanwhile, seven receiving units 10' are placed apart from each other at every 15 degrees starting from the extension line in the direction of magnetic fields of the elastic waves generating unit 10, as indicated by arrows.

Figure 8:
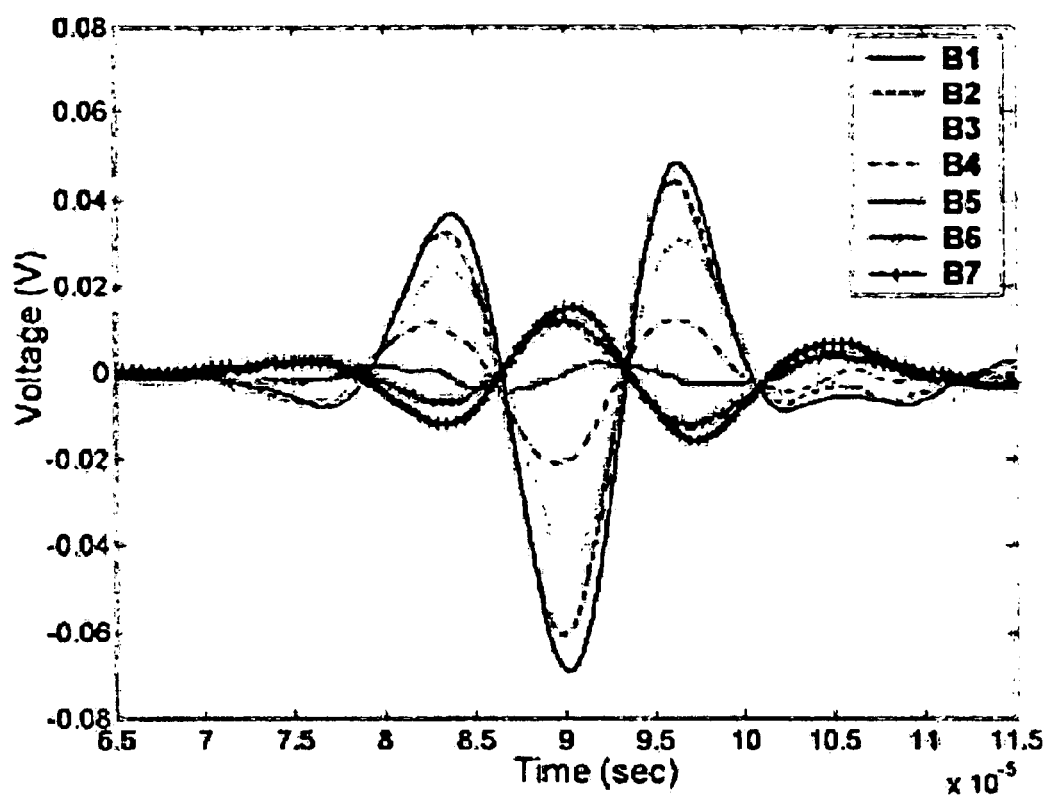
FIG. 8 is a graph showing the data measured in the experiment of FIG. 7.
Figure 9:
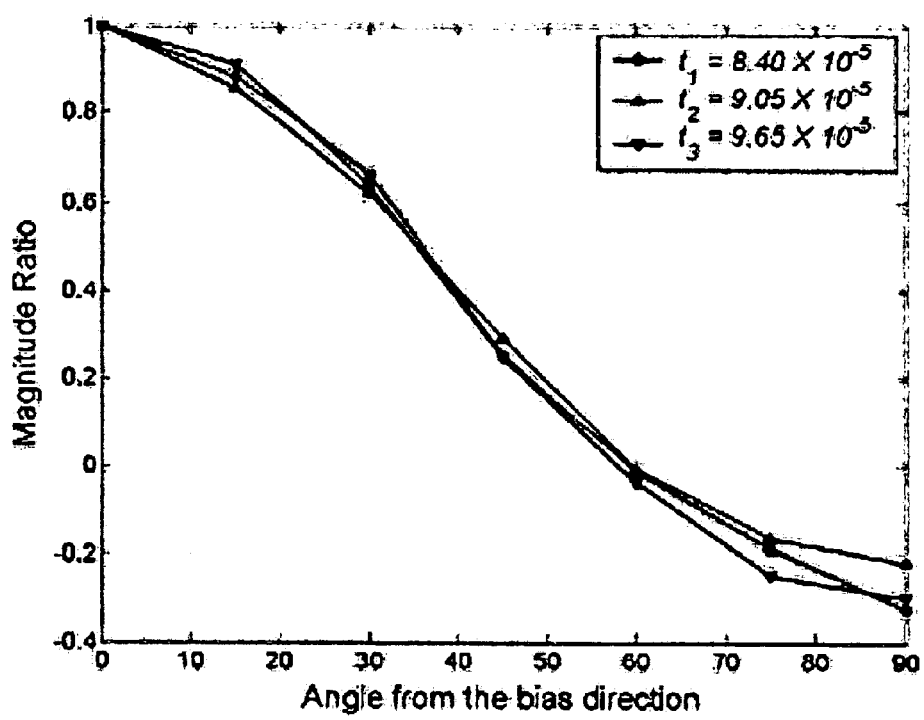
FIG. 9 is a graph showing magnitude ratio measured at every single elastic waves receiving unit.

FIGS. 8 and 9 illustrate signals measured at every single elastic waves receiving unit after supplying alternating currents to the elastic waves generating unit 10 with the arrangement mention above.

FIG. 8 is a graph showing a variation of voltage according to lapse of time. And, FIG. 9 is a graph showing magnitude ratio measured at every single elastic waves receiving unit when magnitude of amplitude received at elastic waves receiving unit placed on extension line in a direction of the bias magnetic field is regarded as "1." The magnitudes of amplitude are measured according to moments when voltage variation in FIG. 8 is a maximum.

As illustrated in FIGS. 8 and 9, when angle between a direction of the bias magnetic field of the elastic waves generating unit and a direction of magnetic field of the elastic waves receiving unit is 60 degrees, there is no variation in voltage. In other words, FIGS. 8 and 9 illustrate that little Lamb wave is generated at an angle of 60 degrees from the direction of magnetic fields of the elastic waves generating unit. Actually only SH waves are transmitted in the direction. Therefore, only SH waves can be detected, when angle between the direction of the bias magnetic field of the elastic waves generating unit and the direction of magnetic field of the elastic waves receiving unit is 60 degrees.

Figure 10:
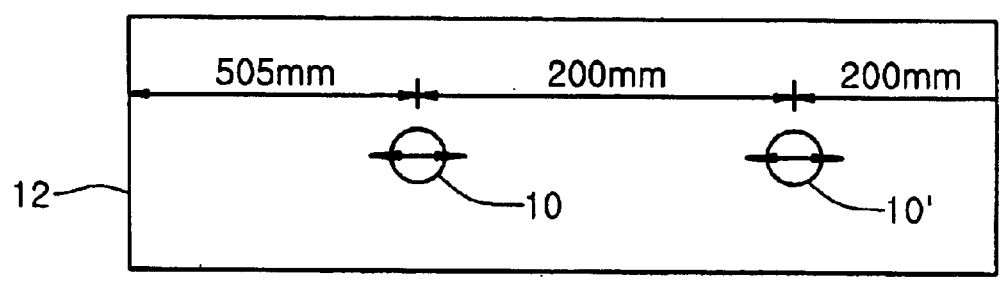
FIG. 10 illustrates an embodiment for measuring Lamb waves on aluminum plate according to the present invention.
Figure 11:
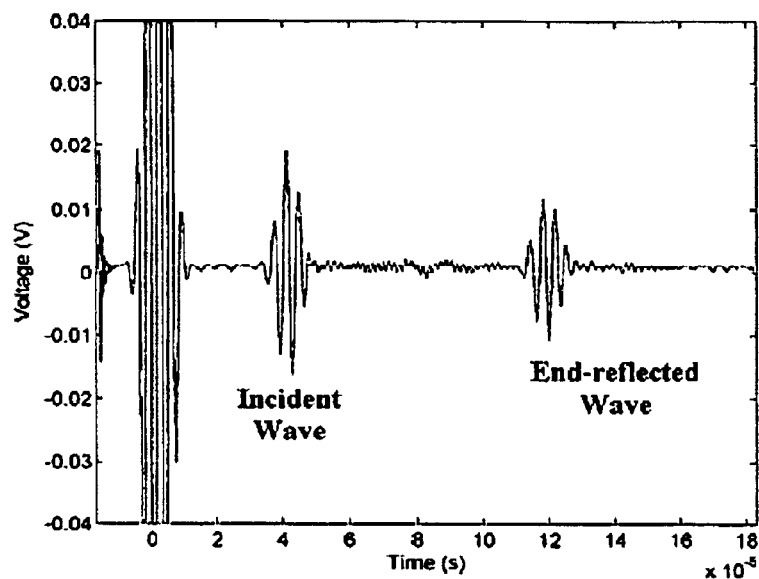
FIG. 11 is a graph showing the data measured in FIG. 10.

FIG. 10 illustrates an embodiment for measuring Lamb waves on aluminum plate according to the present invention and FIG. 11 illustrates data measured from the experimental setup illustrated in FIG. 10.

As illustrated in FIG. 10, two transducers are placed above or on a plate 12. There are two patches on the plate 12 and each transducer is placed above or on the respective patch. The two transducers are placed to set directions of their own magnetic fields equal to a line connecting the two transducers. A first transducer of the two transducers acts as an elastic waves generating unit (transmitter) 10 for generating elastic waves and a second transducer acts as an elastic waves receiving unit (receiver) 10' for receiving the elastic waves. If an electric current is supplied to the elastic waves generating unit 10, ferromagnetic patch of the elastic waves generating unit 10 is deformed according to the magnetostrictive effect. Due to the deformation of the ferromagnetic patch of the elastic waves generating unit 10, elastic waves are generated from the elastic waves generating unit 10 and transmitted to the plate. The elastic waves are transmitted through the plate in all directions. Especially, in a direction of the elastic waves receiving unit 10', Lamb waves are transmitted. The Lamb waves transmitted in the direction of the elastic waves receiving unit 10' deforms ferromagnetic patch, so that magnetic field of the elastic waves receiving unit 10' is varied. The variation of the magnetic field is measured at magnetic field measuring unit (not illustrated) and is illustrated in FIG. 11.

A first peak on left refers to an incident Lamb waves transmitted from the elastic waves generating unit 10 for generating elastic waves, and a second peak on right is a reflected Lamb waves reflected at end part of the plate 12.

Figure 12:
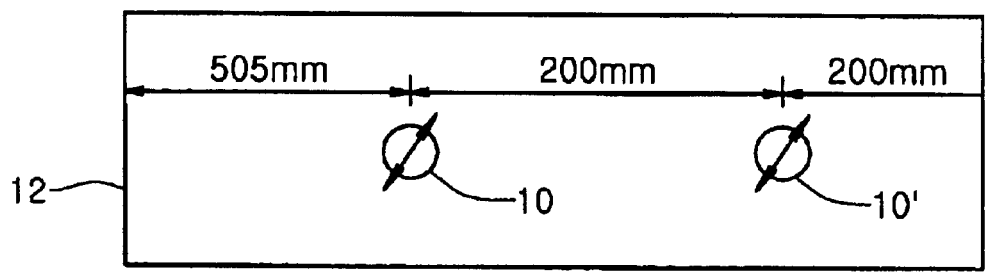
FIG. 12 illustrates an embodiment for measuring SH waves on aluminum plate according to the present invention.
Figure 13:
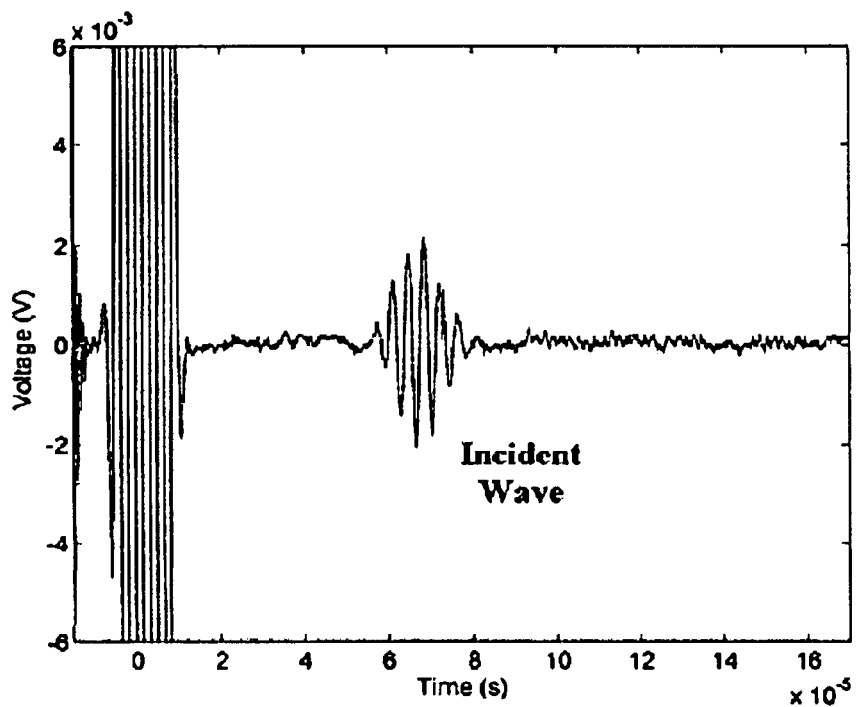
FIG. 13 is a graph showing the data measured in FIG. 12.

FIG. 12 illustrates an embodiment for measuring SH waves on aluminum plate according to the present invention. FIG. 13 is a graph showing data measured in FIG. 12.

As illustrated in FIG. 12, two transducers according to the present invention are placed above or on a plate 12. There are two patches on the plate 12 and each transducer is placed above or on the respective patch. The two transducers are placed to set an angle between a direction of each magnetic field and a line connecting the two transducers equal to 60 degrees. A first transducer acts as an elastic waves generating unit 10 for generating elastic waves and a second transducer acts as an elastic waves receiving unit 10' for receiving the elastic waves. If an electric current is supplied to the elastic waves generating unit 10, ferromagnetic patch of the elastic waves generating unit 10 is deformed according to the magnetostrictive effect. Due to the deformation of the ferromagnetic patch of the elastic waves generating unit 10, elastic waves are generated from the elastic waves generating unit 10 and transmitted to the plate. The elastic waves are transmitted through the plate in all directions. Especially, in a direction of the elastic waves receiving unit 10', SH waves are transmitted.

The SH waves transmitted in the direction of the elastic waves receiving unit 10' deforms ferromagnetic patch of the elastic waves receiving unit 10', so that magnetic field of the elastic waves receiving unit 10' is varied. The variation of the magnetic field is measured at measuring unit (not illustrated) and is illustrated in FIG. 13. A peak illustrated in FIG. 13 is SH waves generated by the elastic waves generating unit 10.

According to the present invention, it is possible to generate and measure Lamb waves and SH waves with one kind of transducer without changing a configuration of an apparatus for structural diagnosis, by using features according to directions of magnetic fields of the transducer illustrated in FIGS. 10 and 12. Such is simply achieved by changing a direction of magnetic field of the transducer.

Figure 14:
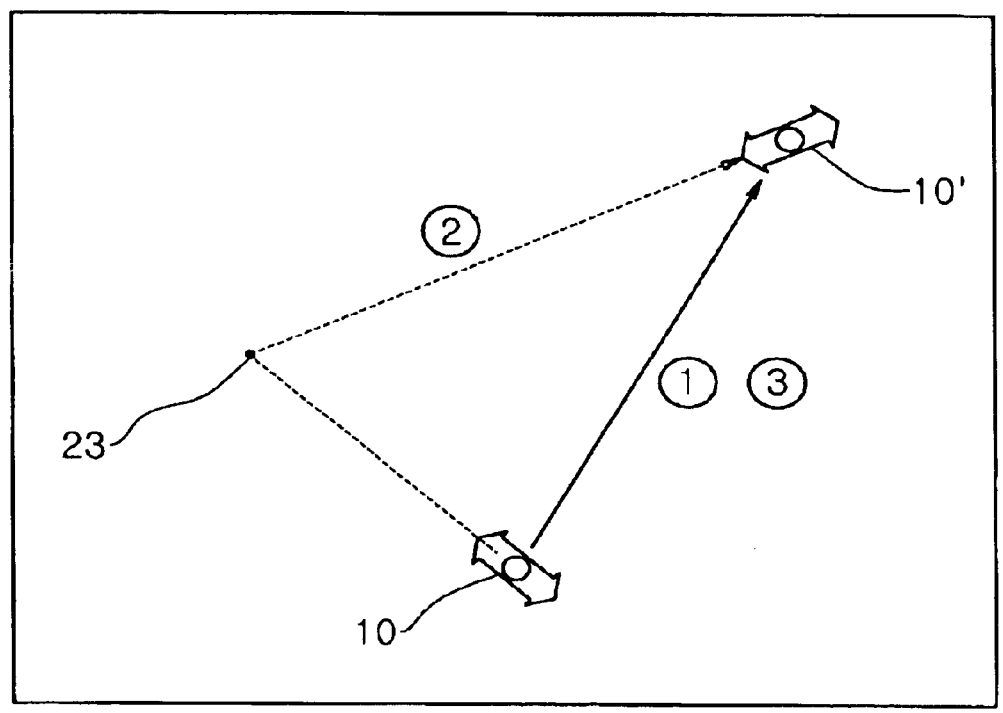
FIG. 14 illustrates a two dimensional inspection using Lamb waves in the apparatus for structural diagnosis according to the present invention.
Figure 15:
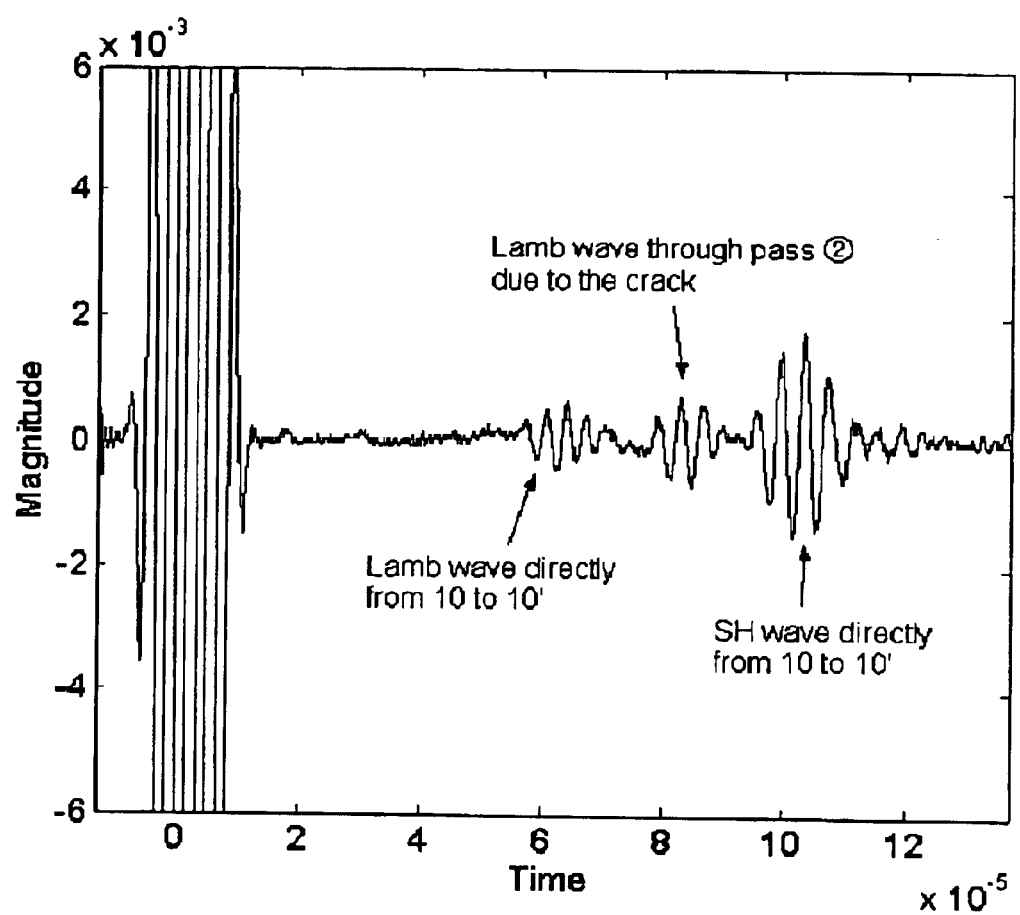
FIG. 15 is a graph showing the data measured by the method shown in FIG. 14.

FIG. 14 illustrates a two dimensional inspection of defects in a plate using an apparatus for structural diagnosis according to the present invention, and FIG. 15 illustrates result measured when a direction of magnetic fields of the elastic waves generating unit 10 for generating elastic waves is aligned toward a defect 23, as illustrated in FIG. 14.

As illustrated in FIG. 14, two transducers according to the present invention are placed on or above a testing plate. A first transducer of those two transducers acts as an elastic waves generating unit 10 for generating elastic waves and a second transducer acts as an elastic waves receiving unit 10' for receiving the elastic waves. If an electric current is supplied to the elastic waves generating unit 10, ferromagnetic patch of the elastic waves generating unit 10 is deformed according to the magnetostrictive effect. Due to the deformation of the ferromagnetic patch of the elastic waves generating unit 10, elastic waves are generated from the elastic waves generating unit 10 and transmitted to the plate.

The elastic waves transmitted in the direction of the elastic waves receiving unit 10' deforms ferromagnetic patch of the elastic waves receiving unit 10', so that magnetic field of the elastic waves receiving unit 10' is varied. It is possible to perform two dimensional inspection of defects in the entire plate by repeatedly measuring magnetic field applied to the elastic waves receiving unit with the direction of magnetic field of the elastic waves generating unit 10 rotating.

Two dimensional inspection of defects in a plate is performed, while changing the direction of magnetic fields of the elastic waves generating unit 10 and elastic waves receiving unit 10', as arranged in FIG. 14.

FIG. 15 illustrates result measured when the directions of magnetic fields of the elastic waves generating unit 10 and the elastic waves receiving unit 10' are aligned toward crack 23 on the plate while changing the direction of magnetic fields of the elastic waves generating unit 10 and elastic waves receiving unit 10'. Herein, the elastic waves receiving unit 10' is placed on a place where angle between the direction of magnetic field of the elastic waves generating unit and a line connecting the elastic waves receiving unit and the elastic waves generating unit is about 60 degrees.

When the magnetic fields of the elastic waves generating unit 10 for generating elastic waves and elastic waves receiving unit 10' for receiving elastic waves are respectively directed toward the crack 23, a peak. in FIG. 15 refers to a signal for Lamb waves directly transmitted to the elastic waves receiving unit 10' from the elastic waves generating unit 10 through a route. in FIG. 14. A signal for reflected Lamb waves from the crack 23 through a route . in FIG. 14 is a peak. of the FIG. 15. A peak. in FIG. 15 refers to a signal for SH waves directly transmitted to the elastic waves receiving unit 10' from the elastic waves generating unit 10 through a route in FIG. 14. Based on such measurement, position of the crack 23 can be detected through finding intersection of extended lines of two magnetic fields.

As described above, the present invention provides a magnetostrictive transducer for stably generating and receiving elastic waves even in a plate made of non-magnetic materials such as aluminum through using the magnetostrictive effect. A magnetic field of the magnetostrictive transducer according to the present invention applied to a patch is generated to be parallel to the patch, so that efficient magnetostrictive effect can be obtained.

According to the present invention, a magnetostrictive transducer using a patch having circular shape or the other shape is used and magnetic field applied to the patch is generated to be parallel to the patch, so that it is easy. to generate SH waves vibrating a particle vertically to the direction of wave propagation in a plane parallel to the plate as well as Lamb waves.

Further, according to the present invention, a direction of magnetic field applied to a patch of a magnetostrictive transducer can be changed, so that it is possible to change a direction of elastic waves propagation by controlling a direction of bias magnetic field. Thus, it is possible to perform two dimensional inspection of defects in a plate without modifying a configuration of an apparatus for structural diagnosis according to the present invention.

Further, according to the present invention, Lamb waves and SH waves in desired directions are generated and measured depending on a direction of bias magnetic field, so that it is possible for one kind of transducer to perform inspection of defects of a plate with various modes of elastic waves.

Although preferred embodiments of the present invention have been described for illustrative purposes, those skilled in the art will appreciate that various modifications, additions and substitutions arc possible, without departing from the scope and spirit of the invention as disclosed in the accompanying claims.

What is claimed as new and desired to be protected by Letters Patent of the United States is:

1. Magnetostrictive transducer comprising:
   a patch having predetermined thickness, the patch being made of ferromagnetic material; and.
   a magnetic field generator for generating magnetic field applied to the patch, the magnetic field generator being placed above the patch,
   wherein the magnetic field generator comprises:
   a main body made of non-magnetic material;
   two magnets for generating bias magnetic field applied to the patch, the magnets being located in upper part of the main body, the magnets being apart from each other; and
   a coil for winding around the magnets,
   and wherein, as an alternating current is supplied to the coil, additional magnetic field applied to the patch is generated, and the bias magnetic field and the additional magnetic field are parallel to the patch,
   and wherein, as an alternating current is supplied to the coil, the patch generates Lamb waves in direction of the magnetic field and shear horizontal (SH) waves in direction forming predetermined angle with the direction of the magnetic field.

2. The magnetostrictive transducer according to claim 1, wherein the magnetic field generator is rotatable to change the directions of the Lamb waves and the SH waves.

3. The magnetostrictive transducer according to claim 1, wherein the patch is a circular patch.

4. The magnetostrictive transducer according to claim 1, wherein the coil is wound around the two magnets in shape of "8."

5. The magnetostrictive transducer according to claim 1, wherein a first magnet of the two magnets puts N pole down and a second magnet of the two magnets puts N pole up, whereby the magnetic fields generated by the two magnets are parallel to the patch.

6. The magnetostrictive transducer according to claim 1, wherein the magnetic field generator is placed on the patch.

7. The magnetostrictive transducer according to claim 1, wherein a change in magnetic field applied to the patch is detected through the magnetic field generator.

8. Apparatus for structural diagnosis using magnetostrictive transducers comprising:
   two magnetostrictive transducers, each of the two magnetostrictive transducers comprising a patch made of ferromagnetic material and a magnetic field generator, placed above the patch, for generating magnetic field applied to the patch;
   a power source for supplying electric currents to the magnetostrictive transducer; and a measuring unit for measuring voltage output of the magnetostrictive transducer, wherein the magnetic field generator comprises: a main body made of non-magnetic material; two magnets for generating bias magnetic field applied to the patch, the magnets being located in upper part of the main body, the magnets being apart from each other; and a coil for winding round the magnets, wherein, as an alternating current is supplied to the coil of a first transducer of the two transducers, the patch generates Lamb waves in direction of the magnetic field and shear horizontal (SH) waves in direction forming predetermined angle with the direction of the magnetic field, wherein, as the patch of the second transducer goes through mechanical deformation due to the Lamb waves or the SH waves from the first transducer, the magnetic field of the second transducer varies and amount of the voltage across the coil of the second transducer varies due to the variation of the magnetic field, and wherein defects of testing plate existing in traveling route of the Lamb waves or the SH waves from the first transducer are detected by the measuring unit's measuring the voltage variation across the coil of the second transducer.

9. The apparatus for structural diagnosis according to claim 8, wherein the magnetic field generators are rotatable to change the directions of Lamb waves and SH waves.

10. The apparatus for structural diagnosis according to claim 8, wherein the patches of the magnetostrictive transducers are circular patches.

11. The apparatus for structural diagnosis according to claim 8, wherein the coil is wound the two magnets in shape of "8."

12. The apparatus for structural diagnosis according to claim 8, wherein a first magnet of the two magnets puts N pole down and a second magnet of the two magnets has N pole up, whereby the magnetic fields generated by the two magnets are parallel to the patch.

13. The apparatus for structural diagnosis according to claim 8, wherein the magnetic field generator is placed on the patch.

* * * * *